United States Patent [19]

Beal et al.

[11] Patent Number: 5,429,630
[45] Date of Patent: Jul. 4, 1995

[54] ABSORBENT ARTICLE AND A METHOD OF REMOVING SAID ARTICLE FROM AN UNDERGARMENT

[75] Inventors: Chantelle M. Beal, Oshkosh; Valerie V. Finch, Neenah; Paul J. Serbiak, Appleton, all of Wis.

[73] Assignee: Kimberly-Clark Corporation, Appleton, Wis.

[21] Appl. No.: 891,387

[22] Filed: May 29, 1992

[51] Int. Cl.⁶ .............................................. A61F 13/15
[52] U.S. Cl. ................................ 604/385.1; 604/387; 604/389
[58] Field of Search ...................... 604/385.1, 386, 387, 604/389, 391, 393, 394, 397

[56] References Cited

U.S. PATENT DOCUMENTS

| D. 247,368 | 2/1978 | Whitehead | D24/51 |
|---|---|---|---|
| D. 247,369 | 2/1978 | Whitehead | D24/51 |
| D. 247,371 | 2/1978 | Whitehead | D24/51 |
| D. 247,372 | 2/1978 | Whitehead | D24/51 |

(List continued on next page.)

FOREIGN PATENT DOCUMENTS

| 0299532A1 | 1/1989 | European Pat. Off. . |
|---|---|---|
| 0301491A1 | 2/1989 | European Pat. Off. . |
| 0314535A1 | 5/1989 | European Pat. Off. . |
| 0337438A1 | 10/1989 | European Pat. Off. . |
| 0345703A1 | 12/1989 | European Pat. Off. . |
| 0347319A1 | 12/1989 | European Pat. Off. . |
| 0359501A2 | 3/1990 | European Pat. Off. . |
| 0389023A2 | 9/1990 | European Pat. Off. . |
| 0424165 | 4/1991 | European Pat. Off. . |
| 0426235A2 | 5/1991 | European Pat. Off. . |
| 0464855 | 1/1992 | European Pat. Off. . |
| 047138 | 2/1992 | European Pat. Off. . |
| 0471385A1 | 2/1992 | European Pat. Off. . |
| 0471587A1 | 2/1992 | European Pat. Off. . |
| 2268479 | 11/1979 | France . |
| 3319421A1 | 11/1984 | Germany . |
| 40-36391 | 12/1965 | Japan . |
| 46-12554 | 5/1971 | Japan . |
| 48-43500 | 6/1973 | Japan . |
| 48-59395 | 7/1973 | Japan . |
| 48-73497 | 9/1973 | Japan . |
| 49-18398 | 2/1974 | Japan . |
| 49-25294 | 3/1974 | Japan . |
| 50-10718 | 4/1975 | Japan . |
| 50-100399 | 8/1975 | Japan . |
| 52-117394 | 3/1976 | Japan . |
| 54-154696 | 10/1979 | Japan . |
| 55-16135 | 2/1980 | Japan . |
| 57-20172 | 4/1982 | Japan . |
| 60-158828 | 10/1985 | Japan . |
| 61-51810 | 4/1986 | Japan . |
| 61-154931 | 9/1986 | Japan . |
| 59-225058 | 5/1989 | Japan . |
| 2048684 | 12/1980 | United Kingdom . |
| WO92/07536 | 5/1992 | WIPO . |
| WO92/07537 | 5/1992 | WIPO . |

OTHER PUBLICATIONS

Utilization of Water–Absorbent Polymers in Hygienic Field—Hygienic Product Laboratories Water–Absorbent Resin Utilization And Future Trends I (Japanese) 1988.

Highly Absorbent Polymers and Application in Hygienic Materials—Hygienic Products Laboratories (Japanese) 1987.

Primary Examiner—Mary Beth O. Jones
Attorney, Agent, or Firm—Thomas J. Connelly

[57] ABSTRACT

An absorbent article is disclosed along with a method of removing the absorbent article from an undergarment. The absorbent article has a liquid-permeable cover, a liquid-impermeable baffle, and an absorbent positioned therebetween to form a pad. The pad has a central portion, longitudinally-extending sides, and a pair of relatively stiff tabs extending laterally outward from the longitudinal sides. The pad has a body-facing surface and a garment-facing surface. The absorbent article further includes adhesive for securing the pad to the crotch portion of an undergarment. The adhesive is secured on the garment-facing surface of the pad and is present on each of the tabs. Release paper covers the adhesive.

27 Claims, 6 Drawing Sheets

U.S. PATENT DOCUMENTS

| | | | |
|---|---|---|---|
| D. 2,534,423 | 11/1979 | Roeder | D24/51 |
| D. 253,424 | 11/1979 | Roeder | D24/51 |
| D. 253,425 | 11/1979 | Roeder | D24/51 |
| D. 253,550 | 11/1979 | Roeder | D24/51 |
| D. 253,674 | 12/1979 | Whitehead | D24/51 |
| D. 274,361 | 6/1984 | Whitehead | D24/51 |
| D. 274,362 | 6/1984 | Whitehead | D24/51 |
| D. 276,072 | 10/1984 | Whitehead | D24/51 |
| D. 276,183 | 10/1984 | Whitehead | D24/51 |
| D. 276,184 | 10/1984 | Whitehead | D24/51 |
| D. 276,368 | 11/1984 | Whitehead | D24/51 |
| 2,154,332 | 4/1939 | Hirsch | 128/292 |
| 2,408,508 | 10/1946 | Canavan | 128/290 |
| 2,787,271 | 4/1957 | Clark . | |
| 3,315,677 | 4/1967 | Tyrrell, Jr. | 128/288 |
| 3,397,697 | 8/1968 | Rickard . | |
| 3,400,718 | 9/1968 | Saijo | 128/291 |
| 3,805,790 | 4/1974 | Kaczmarzyk et al. | 128/290 R |
| 3,881,490 | 5/1975 | Whitehead et al. | 128/287 |
| 3,888,255 | 6/1975 | Shah et al. | 128/290 R |
| 3,897,783 | 8/1975 | Ginocchio | 128/290 R |
| 3,913,580 | 10/1975 | Ginocchio | 128/290 W |
| 4,055,184 | 10/1977 | Karami | 128/287 |
| 4,079,739 | 3/1978 | Whitehead | 128/290 R |
| 4,100,324 | 7/1978 | Anderson et al. | 428/288 |
| 4,144,886 | 3/1979 | Holst et al. | 128/284 |
| 4,217,901 | 8/1980 | Bradstreet et al. | 128/290 R |
| 4,285,343 | 8/1981 | McNair . | |
| 4,315,507 | 2/1982 | Whitehead et al. | 128/287 |
| 4,324,246 | 4/1982 | Mullane et al. | 128/287 |
| 4,327,732 | 5/1982 | Thinnes | 128/290 R |
| 4,333,465 | 6/1982 | Wiegner | 128/290 R |
| 4,333,466 | 6/1982 | Matthews | 128/290 R |
| 4,347,092 | 8/1982 | Hlaban et al. | 156/227 |
| 4,364,992 | 12/1983 | Ito et al. | 428/283 |
| 4,425,130 | 1/1984 | DesMarais | 604/389 |
| 4,496,359 | 1/1985 | Pigneul | 604/387 |
| 4,526,825 | 7/1985 | Whitehead | 428/74 |
| 4,576,597 | 3/1986 | Hlaban | 604/390 |
| 4,589,876 | 5/1986 | Van Tilburg | 604/385 R |
| 4,608,047 | 8/1986 | Mattingly | 604/387 |
| 4,655,759 | 4/1987 | Romans-Hess et al. | 604/385 R |
| 4,687,478 | 8/1987 | Van Tilburg | 604/387 |
| 4,701,178 | 10/1987 | Glaug et al. | 604/387 |
| 4,710,186 | 12/1987 | DeRossett et al. | 604/383 |
| 4,738,676 | 4/1988 | Osborn, III | 604/385 R |
| 4,755,413 | 7/1988 | Morris | 428/138 |
| 4,759,754 | 7/1988 | Korpman | 604/387 |
| 4,762,521 | 8/1988 | Roessler et al. | 604/383 X |
| 4,773,905 | 9/1988 | Molee et al. | 604/378 |
| 4,790,838 | 12/1988 | Pigneul et al. | 604/366 |
| 4,798,601 | 1/1989 | Shirose et al. | 604/368 |
| 4,798,603 | 1/1989 | Meyer et al. | 604/378 |
| 4,834,739 | 5/1989 | Linker, III et al. | 604/385.1 |
| 4,862,574 | 9/1989 | Seidy | 29/415 |
| 4,900,319 | 2/1990 | Richwine | 604/385.1 |
| 4,900,320 | 2/1990 | McCoy | 604/387 |
| 4,911,701 | 3/1990 | Mavinkurve | 604/385.2 |
| 4,917,697 | 4/1990 | Osborn, III et al. | 604/387 |
| 4,936,839 | 6/1990 | Molee et al. | 604/378 |
| 4,940,462 | 7/1990 | Salerno | 604/387 |
| 4,963,139 | 10/1990 | Dabroski | 604/378 |
| 5,007,906 | 4/1991 | Osborn, III et al. | 604/385.1 |
| 5,011,480 | 4/1991 | Gossens et al. | 604/385.1 |
| 5,037,418 | 8/1991 | Kons et al. | 604/387 |
| 5,092,860 | 3/1992 | Pigneul | 604/380 |
| 5,154,715 | 10/1992 | Van Iten | 604/387 |

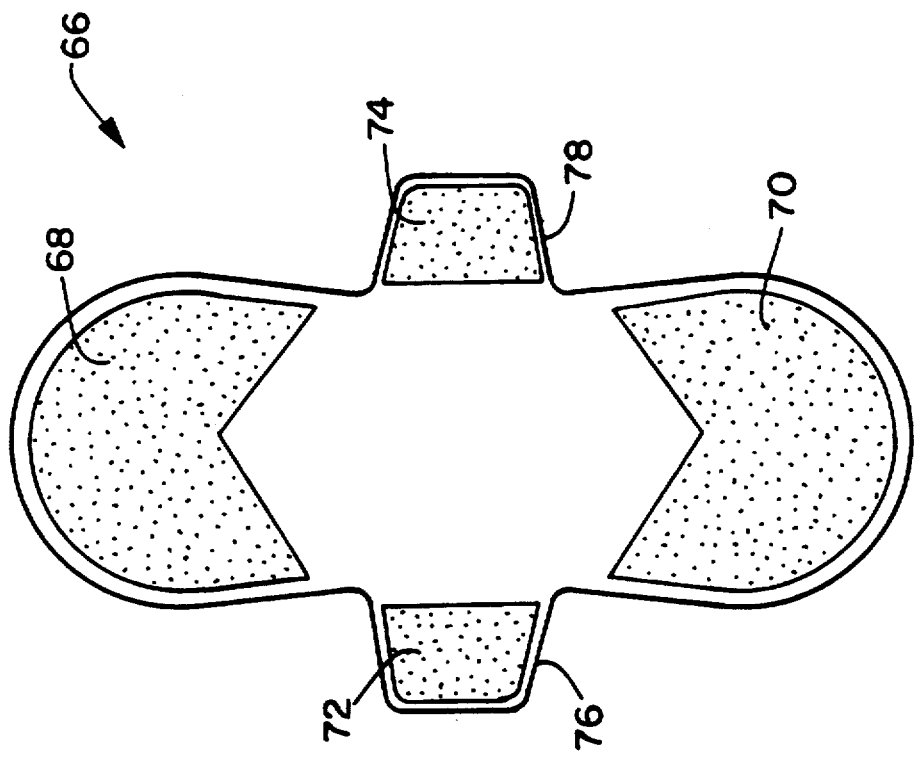
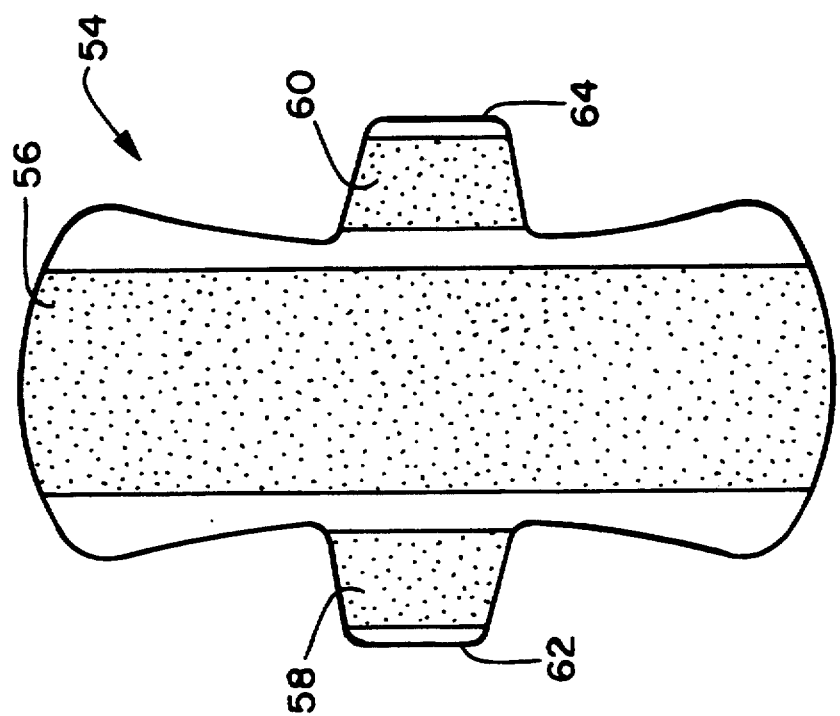

ABSORBENT ARTICLE AND A METHOD OF REMOVING SAID ARTICLE FROM AN UNDERGARMENT

FIELD OF THE INVENTION

This invention relates to an absorbent article and a method of removing the article from an undergarment. More specifically, this invention relates to an absorbent article having a central absorbent portion with longitudinally-extending sides and a pair of relatively stiff tabs extending laterally outward from the longitudinal sides. Adhesive areas are present on the central portion and the tabs and are covered by a single piece of release paper. The importance of using an absorbent article with relatively stiff tabs is to ensure that, when the release paper has been removed, the tabs will not appreciably droop or fold downward. This will prevent the adhesive areas on the tabs from prematurely contacting the central portion before the article is secured to an undergarment.

BACKGROUND OF THE INVENTION

Absorbent articles such as sanitary napkins, catamenial pads, Feminine pads, panty liners, panty shields and incontinence garments are devices which are designed to be worn adjacent to a woman's pudendum to absorb body fluids such as menses, blood, urine, and other excrements. Sanitary napkins are designed to be worn during the menstrual period, while panty liners and panty shields can be worn prior to, during, or after the menstrual period. Incontinence garments can be worn at any time to absorb urine and other body fluids. Some women use incontinence garments to absorb menses. Many times, panty liners and panty shields are worn in conjunction with a tampon, which is an internal device designed to also absorb body fluids. A difference between sanitary napkins and panty liners is the amount of fluid which each can absorb. Sanitary napkins are generally larger in size, usually thicker, and are capable of absorbing a greater quantity of body fluids.

It has been known for some time that absorbent articles can contain a pair of side flaps which extend laterally outward from the longitudinal sides of the central absorbent. Such flaps can prevent staining of the undergarment. Some flaps are designed to wrap around the undergarment and attach to each other so as to hold the article securely in place.

One of the early patents to teach the use of flaps on a sanitary napkin was U.S. Pat. No. 2,787,271 to Clark. U.S. Pat. No. 3,397,697 to Rickard and U.S. Pat. No. 4,285,343 to McNair provided improvements wherein the flaps overlapped so as to hold the sanitary napkin securely to the undergarment. Since 1953, many versions of sanitary napkins with panty-gathering flaps have been patented. U.S. Patent 4,608,047 to Mattingly, U.S. Pat. No. 4,900,320 to McCoy, and U.S. Pat. Nos. 4,589,876, and 4,687,478, both to Van Tilburg, teach the use of flexible flaps.

In addition to the above patents, manufacturers have been perfecting die-cutting operations to make absorbent articles. U.S. Pat. No. 4,079,739 to Whitehead and U.S. Pat. No. 4,862,574 to Seidy teach die cutting absorbent articles.

A review of the prior art shows that absorbent articles, which contain a pair of outwardly-extending flaps require separate and distinct strips of release paper to cover the distinct adhesive areas. A reason for this is that adhesive is an expensive component of the article. Therefore, manufacturers have tended to use only what was needed. This factor has caused the adhesive to be applied in separate and discrete areas instead of over the entire garment-facing surface. A second reason why separate strips of release paper have been used in the past is that manufacturers have made the flaps very flexible. The use of a single piece of release paper was frowned upon because, once the release paper was removed, the flaps would tend to fold down and the adhesive on the flaps could contact another portion of the article before the article was positioned in the crotch portion of an undergarment. Once the adhesive is attached to another portion of the article, it is difficult to remove the flap without damaging or tearing either the flap or the article. This would then prevent the consumer from properly applying the absorbent article to the crotch portion of the undergarment. Such action could cause the user to become frustrated. Accordingly, manufacturers have stayed away from using a single piece of release paper on absorbent articles with flaps.

One manufacturer of absorbent articles with flaps uses three separate pieces of release paper. This manufacturer has printed instructions on the package to teach the consumer how to remove the release paper. The release paper positioned over the central adhesive is first removed and the article is attached to the inner surface of the crotch portion of an undergarment. The release paper covering the adhesive on one of the flaps is then removed, and that flap is attached to an exterior surface of the undergarment. The consumer then removes the last piece of release paper from the opposite flap, and that flap is then attached to the exterior surface of the undergarment. If this procedure is not followed correctly, the adhesive usually attaches to another portion of the absorbent article and the article can be ruined before it can be applied.

One attempt to resolve this problem is taught in U.S. Pat. No. 5,011,480 to Gossens et al. This patent teaches a feminine pad having a pair of outwardly-extending flaps which are covered by a frictional material. The frictional material holds the article securely to an undergarment but does not adhere to itself.

Now, an absorbent article has been invented which has a pair of relatively stiff tabs which will not appreciably droop or fold downward and allow the adhesive areas on the tabs to prematurely contact another portion of the article.

SUMMARY OF THE INVENTION

Briefly, this invention relates to an absorbent article having a liquid-permeable cover, a liquid-impermeable baffle, and an absorbent positioned therebetween to form a pad. The pad has a central portion, longitudinally-extending sides, and a pair of relatively stiff tabs extending laterally outward from the longitudinal sides. The pad has a body-facing surface and a garment-facing surface. The absorbent article further includes adhesive for securing the pad to the crotch portion of an undergarment. The adhesive is secured on the garment-facing surface of the pad and can be present on the central portion as well as on each of the tabs. A single piece of release paper covers all of the adhesive.

The general object of this invention is to provide an absorbent article having a pair of relatively stiff tabs extending laterally outward from a central portion thereof. A more specific object of this invention is to provide an absorbent article with a pair of relatively stiff tabs which do not fold downward under their own weight.

Another object of this invention is to provide an absorbent article with a pair of relatively stiff tabs which extend laterally outward from a central portion thereof and wherein all of the garment-attachment adhesive is covered by a single piece of release paper.

A further object of this invention is to provide an absorbent article which can be inexpensively produced by a die-cut operation wherein both the release paper and the absorbent pad have coterminous exterior peripheries.

Still another object of this invention is to provide a simple method of removing the absorbent article from the crotch portion of an undergarment after the absorbent article has absorbed a certain quantity of body fluid.

Still further, an object of this invention is to provide an absorbent article with a pair of relatively stiff tabs extending laterally outward from a central portion thereof, and said tabs do not droop downward an appreciable amount once the release paper has been removed.

Other objects and advantages of the present invention will become more apparent to those skilled in the art in view of the following description and the accompanying drawings.

BRIEF DESCRIPTION OF THE DRAWINGS

FIG. 4 is a bottom view of an absorbent article showing three separate and distinct bands of adhesive, one spanning the length of the central portion and the other two spanning the length of the laterally-extending tabs.

FIG. 5 is a bottom view of an absorbent article showing four separate and distinct areas of garment-attachment adhesive with the central portion of the absorbent article being free of adhesive.

DETAILED DESCRIPTION OF THE PREFERRED EMBODIMENTS

Figure 1:
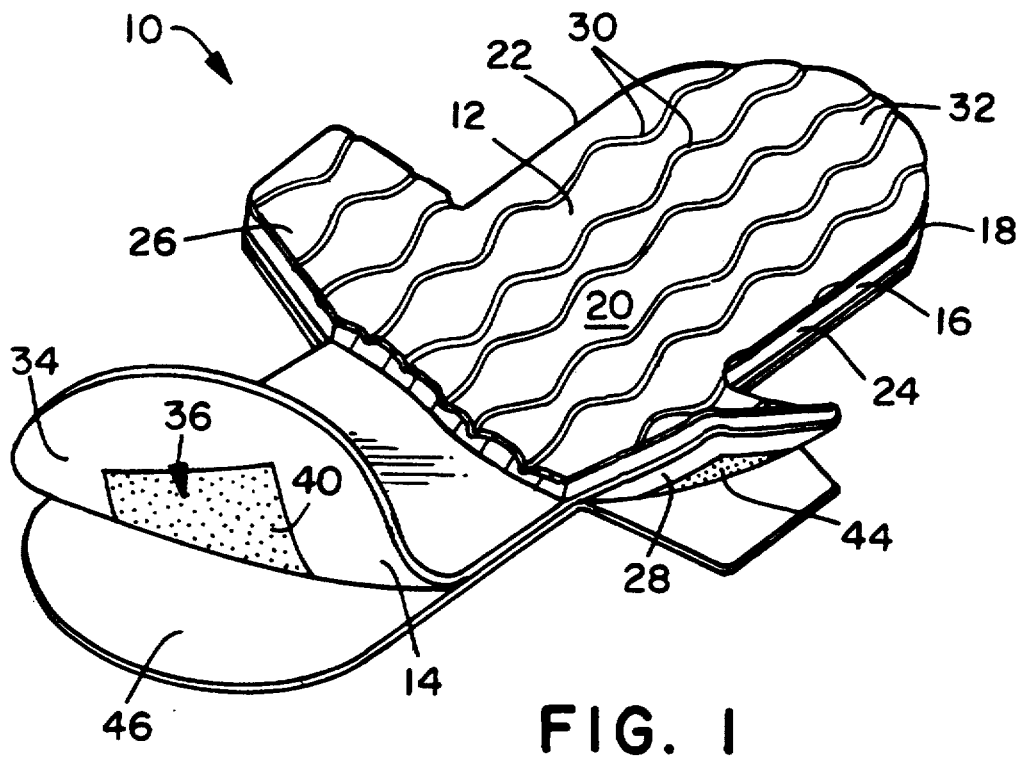
FIG. 1 is a perspective view of an absorbent article having a central portion with a pair of relatively stiff tabs extending laterally outwardly therefrom.

Referring to FIG. 1, an absorbent article 10 is shown which is designed to be worn by a woman to absorb body fluids such as menses, blood, urine, and other excrements. The absorbent article 10 can be a sanitary napkin, a panty liner, a panty shield, an incontinent garment, etc. A sanitary napkin is designed to absorb a greater quantity of fluid than a panty liner or panty shield. A sanitary napkin is usually longer, wider, and thicker than a panty liner and may contain a superabsorbent or other type of material, such as peat moss, which can increase its absorbent capacity. Sanitary napkins can have a length of from about 6 inches to about 13 inches (about 152 mm. to about 330 mm.), a width of about 2 inches to about 5 inches (about 51 mm. to about 127 mm.) and a thickness of about 0.25 mm to about 25 mm. The sanitary napkin can have a rectangular shape, an hourglass shape, an oval shape, a racetrack shape, etc.

Panty liners, on the other hand, are relatively thin and small and can, but usually do not, contain a superabsorbent. A panty liner can have a length of from about 6 inches to about 10 inches (about 152 mm to about 254 mm), a width of about 2 inches to about 3 inches (about 51 mm to about 76 mm), and a thickness of about 1.3 mm to about 3.6 mm. Panty liners can be made in various configurations but, until now, none have been made with laterally-extending tabs.

Incontinent garments are usually equal to or larger than sanitary napkins. Incontinent garments can have a length of from about 6 inches to about 33 inches (152 mm to 838 mm), a width of about 2.5 inches to about 30 inches (about 64 mm to 762 mm) and a thickness of about 19 mm to about 76 mm. Incontinent garments commonly have a rectangular or hourglass shape.

The absorbent article 10 can include a liquid-permeable cover 12, a liquid-impermeable baffle 14 and an absorbent 16 positioned therebetween. The cover 12 can be formed of a nonwoven material, such as spunbond. The baffle 14 can be formed from a thin polyethylene film. The cover 12 and the baffle 14 can be eliminated, and the function of these two layers can be performed by other means. For example, the top surface of the absorbent 16 can serve as the cover, and an adhesive coating or a foam layer can replace the baffle.

The absorbent 16 has a body-facing surface and a garment-facing surface. The absorbent 16 can be a hydrophilic material formed from various types of natural or synthetic fibers including cellulose fibers, surfactant treated meltblown fibers, wood pulp fibers, regenerated cellulose or cotton fibers, or a blend of pulp and other fibers. A preferred material is coform. Coform is an air-formed blend of meltblown fibers and staple or pulp fibers. The formation of such material is disclosed in U.S. Pat. No. 4,100,324 to Anderson et al. which is incorporated by reference and made a part hereof. A coform mixture of 70 percent cellulose fibers, with 30 percent polypropylene meltblown fibers, works well.

The absorbent 16 can also contain thermoplastic polymers which can be permanently deformed by the application of heat and pressure. Such materials include polypropylene, nylon, polyethylene, polyesters, etc. Typical of such materials are bonded carded webs, meltblown and spunbond fabrics.

The absorbent 16 can further contain a hydrocolloidal material, commonly referred to as a superabsorbent. The hydrocolloidal material can be a hydrogel-forming polymer composition which is water insoluble, slightly crosslinked, and partially neutralized.

The cover 12, baffle 14, and absorbent 16 are sandwiched together to form a pad 18. The pad 18 includes a central portion 20 with longitudinally-extending sides 22 and 24. The central portion 20 can be formed in various configurations including an elongated oval, an hourglass, a racetrack or a rectangular configuration. The sides 22 and 24 can be either linear or non-linear so that the pad 18 can have various configurations. For example, the pad 18 can have a rectangular, racetrack, hourglass, or an oval-shaped configuration. Extending outward from each of the respective longitudinal sides 22 and 24 are a pair of relatively stiff tabs 26 and 28. The tabs 26 and 28 can have any desired configuration, but a rectangular or trapezoidal configuration work well. When a trapezoidal shape is used, the sides of the tabs can taper inward as they progress toward the distal end of the tab at an angle of about 1 degree to about 25 degrees, preferably about 12 degrees. The taper is measured from a line drawn perpendicularly to the longitudinal center line of the article. The tabs 26 and 28 can have a surface area of about 1.2 in.$^2$ (7.7 cm$^2$). The tabs 26 and 28 have a length, measured parallel to the longitudinal axis of the absorbent article 10, and a width, measured parallel to the transverse axis of the absorbent article 10. The length of each tab can be measured from the middle of the arcuate segment on one side of the tab to the middle of the arcuate segment on the opposite side of the tab. The arcuate segments join the sides of each tab 26 and 28 to the longitudinally-extending sides 22 and 24 of the absorbent article 10. The length of each tab 26 and 28 should be between about 0.75 inches to about 2 inches (about 19 mm to about 51 mm), preferably about 1.5 inches (38 mm). The width of each tab 26 and 28 can be between about 0.5 inches to about 1.5 inches (about 13 mm to about 38 mm), preferably about 1 inch (25.4 mm).

On a sanitary napkin, the length of the tab is less than about 15 percent of the total length of the article, more preferably less than about 10 percent of the length of the article. For a panty liner, the length of the tab can be less than about 25 percent of the total length of the article, and more preferably less than about 20 percent of the length of the article. For example, on a sanitary napkin having a length of about 8.5 inches to about 11 inches (about 216 mm to about 279 mm), as measured along its longitudinal axis, the tab can have a length of about 1.5 to about 2 inches (about 38 to about 51 mm). On a panty liner having a length of about 6 inches to about 7.5 inches (152 mm to about 191 mm), the tab can have a length of about 1.5 inches to about 1.75 inches (38 mm to about 45 mm).

It should be noted that the pad 18 has a uniform thickness throughout and, therefore, the central portion 20 has the same thickness as the tabs 26 and 28. This enables the pad 18 to be die cut during manufacture from a large sheet of laminated material.

The pad 18 can contain a plurality of embossed areas 30. In FIG. 1, the embossed areas 30 are shown as sinusoidal lines formed parallel to the longitudinal axis of the article 10. The embossed areas 30 can add integrity to the article 10 by securing the cover 12 to the absorbent 16. The use of embossed lines gives an indication of ripples, or waves, which some consumers tend to associate with fluid absorption. The embossed areas 30 can be evenly spaced throughout the width of the article 10 and can be present in both the central portion 20 and in each of the tabs 26 and 28. The embossed areas 30 can also be in the form of dots, flowers, etc.

The embossed lines 30 can be formed by running a laminate material through the nip of two rolls, the bottom row being a pressure roll and the top roll being an embossing roll. The embossment will cause the cover 12 to be pinched down into the absorbent 16 and thereby assist the article 10 in being held together.

The pad 18 is formed out of a large sheet of laminate material which comprises a cover 12, baffle 14, and absorbent 16. The pad 18 can be die cut from this sheet of material and will have a body-facing surface 32 and a garment-facing surface 34. The body-facing surface 32 can be formed by the liquid-permeable cover 12, and the garment-facing surface 34 can be formed by the liquid-impermeable baffle 14.

Figure 2:
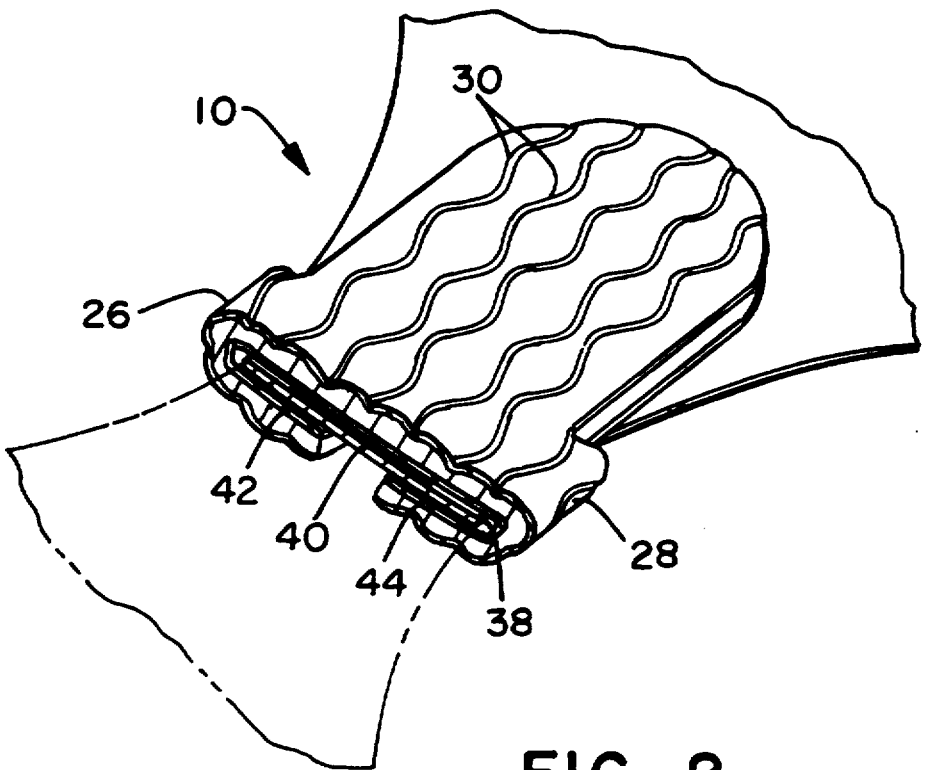
FIG. 2 is a cross-sectional view of an absorbent article applied to the crotch portion of an undergarment.

Referring to FIG. 2, the absorbent article 10 further includes attachment means 36 secured to the garment-facing surface 34. The attachment means 36 can be a garment-attachment adhesive which provides a means for removably securing the pad 18 to the crotch portion of an undergarment 38. A garment attachment adhesive which works well is adhesive NS34-5516 which is commercially available from National Starch Company, located at 10 Finderne Ave., Bridgewater, N.J. 08807.

The attachment means 36 can include an adhesive 40 located on the central portion 20 and adhesive 42 and 44, each located on one of the tabs 26 and 28, respectively. The adhesive 42 and 44 should cover an area of at least 0.5 square inches of each tab 26 and 28, and more preferably at least 50% of each tab 26 and 28. The particular configuration and design of the attachment means 36 can vary.

Referring again to FIG. 1, the absorbent article 10 further includes a single piece of release paper 46 covering the attachment means 36. The release paper 46 and the pad 18 can have coterminous exterior peripheries thereby facilitating a die-cut operation during manufacture. It is also possible to cut the release paper such that it covers all of the adhesive but has a configuration which lies within the outer periphery of at least a portion of the pad 18. For example, the release paper could run the length of the article 10 but be narrower than the overall width of the article 10. The release paper could also be cut larger than the pad 18, for example, having an outlying portion at one end so that the consumer could grasp the release paper and easily remove it from the pad 18.

The absorbent article 10 is designed to be die cut from a sheet of laminate material including: the cover 12, the baffle 14, the absorbent 16, the attachment means 36, and the release paper 46. The die-cutting operation enables the manufacturer to produce the absorbent article 10 efficiently and economically. Lower production costs could be passed on to the consumer.

Until now, most manufacturers of absorbent articles, having a pair of flaps extending laterally outward from the central portion, have used multiple strips of release paper to cover the adhesive areas. One reason for this was the presence of flexible flaps. Flexible flaps tend to droop downward and inward from the body-facing surface. If one piece of release paper was used, one could visualize occasions where the adhesive on the tabs would contact the adhesive on the central portion before the user could apply the article to the crotch portion of an undergarment. Once the adhesive on the tabs contacts the adhesive on the central portion, it is very difficult to pull the members apart without tearing the flaps or damaging the absorbent article.

The present absorbent article 10 differentiates over current commercially available products in that, when the release paper 46 is removed, the relatively stiff tabs 26 and 28 tend to maintain their original position. That is, the body-facing surface 32 of the pad 18 is approximately flat, and there is no droop to the tabs 26 and 28. The stiffness of the tabs 26 and 28 limit droop from occurring. If any droop does occur when the release paper is removed, it is limited to about 25 degrees, preferably less than about 15 degrees, relative to the central portion 20 of the body-facing surface 32. By making the tabs 26 and 28 relatively stiff, one can be assured that, when the release paper 46 is removed, the adhesives 42 and 44 located on each of the tabs 26 and 28 will not come into contact with the adhesive 40 or another portion of the article 10. This is an improvement over the prior art.

Figure 3:
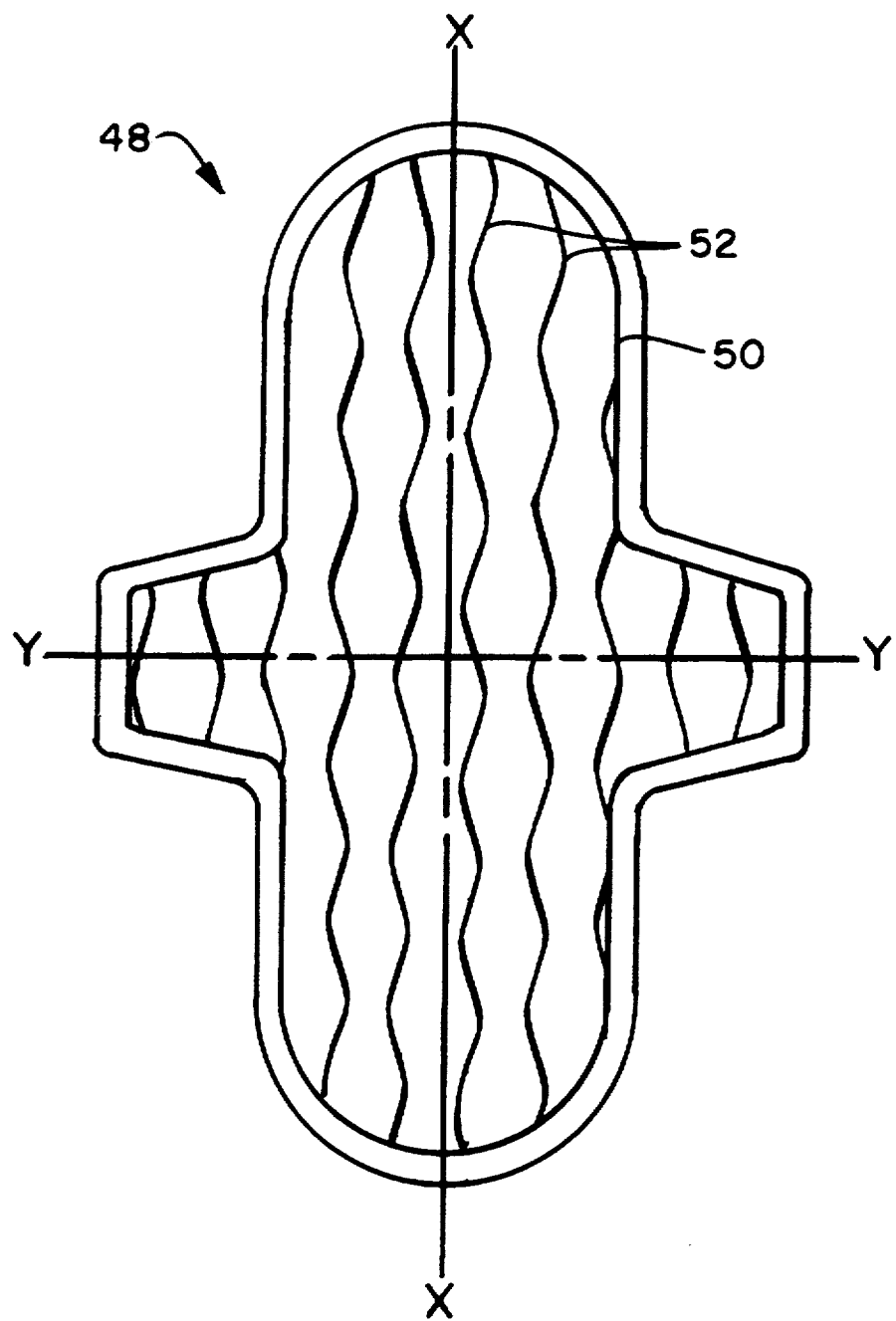
FIG. 3 is a top view of an absorbent article showing longitudinally-embossed lines and a continuous peripheral embossed line located inward from the exterior periphery of the article.

Referring to FIG. 3, an absorbent article 48, such as a sanitary napkin or panty liner is shown. The absorbent article 48 is similar in construction to that discussed in FIG. 1 except that it includes a continuous embossed line 50 formed from about 1/64 to about ½ inch (about 0.4 mm to about 13 mm) inward from the exterior periphery of the absorbent article 48. The embossed line 50 provides integrity between the cover and the absorbent and is advantageous in holding the article together when it is being removed from the crotch portion of an undergarment. The absorbent article 48 has a racetrack configuration with a longitudinal axis designated X—X and a transverse axis designated Y—Y. The absorbent article 48 also contains a plurality of sinusoidal embossed lines 52 which extend lengthwise across the article 48 with respect to the longitudinal axis X—X. The embossed lines 52 do not extend beyond the peripheral embossed line 50. When the absorbent article 48 is a sanitary napkin, it can have a surface area of less than about 30 in.$^2$ (194 cm$^2$), preferably less than about 25 in.$^2$ (161 cm$^2$). When the absorbent article 48 is a panty liner, the surface area can be less than about 20 in.$^2$ (129 cm$^2$).

When the absorbent article 48 is a sanitary napkin, it can have a basis weight of less than about 400 grams per square meter, preferably less than about 300 grams per square meter, and most preferably less than about 250 grams per square meter. For a panty liner, the basis weight can be less than about 200 grams per square meter and preferably about 190 grams per square meter.

Referring to FIGS. 4–7, several different adhesive arrangements for attaching the absorbent article to the crotch portion of an undergarment are shown. In FIG. 4, a lobed-shaped, absorbent article 54 is shown having three separate and discrete areas of garment-attachment adhesive. The absorbent article 54 contains a wide band of adhesive 56 which runs continuously along the length thereof. The absorbent article 54 also contains two narrower bands of garment adhesive 58 and 60 secured to laterally extending tabs 62 and 64. The bands of adhesive 58 and 60 should cover at least 50 percent of the surface area of each tab, more preferably at least about 60 percent, and most preferably from about 85 to about 100 percent of the surface area of each tab. The adhesive 58 and 60 spans the length of each tab 62 and 64, respectively. It should be noted that the amount of adhesive applied to each of the tabs 62 and 64 can vary depending upon the strength of the adhesive, the thickness of the adhesive, as well as the type of material the adhesive will contact. A single piece of release paper covers the adhesive areas 56, 58 and 60. However, the release paper can have a width which only extends to the outside edge of the tabs 62 and 64.

Referring to FIG. 5, an hourglass-shaped absorbent article 66 is shown having four separate and distinct areas of garment-attachment adhesive. Two areas of adhesive 68 and 70 are positioned at opposite ends of the absorbent article 66. The adhesive can be applied to the ends by printing the adhesive onto the garment-facing surface of the absorbent article 66. Two other areas of adhesive 72 and 74 are located on laterally-extending tabs 76 and 78 and cover approximately the entire surface area of each tab. In this design, one will notice that the entire central portion of the garment-facing surface of the absorbent article 66 is free of adhesive. This is a feature which is different from the prior art. Such a configuration may be advantageous with undergarments having a very narrow crotch. By placing the adhesive at the ends of the article, one can obtain a secure fit without having to apply the adhesive over the entire length of the article.

Figure 6:
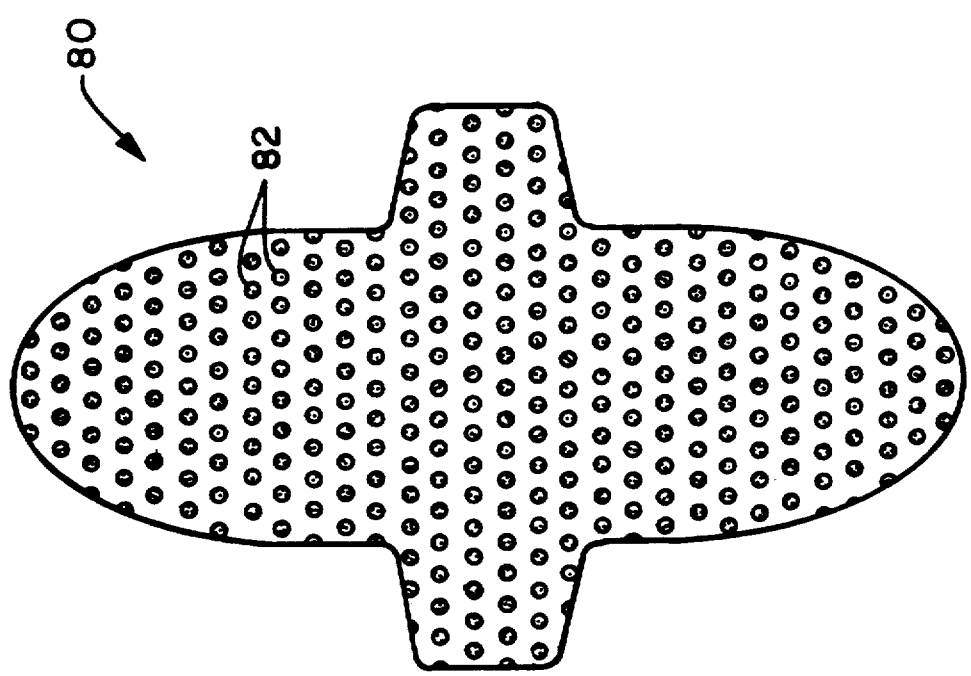
FIG. 6 is a bottom view of an absorbent article showing a continuous dot pattern of adhesive.

Referring to FIG. 6, an absorbent article 80 is shown having a oval shape with a pair of relatively stiff tabs extending laterally outward from the longitudinal sides. The absorbent article 80 contains a dot pattern of garment-attachment adhesive 82 which covers the entire garment-facing surface. Such a dot pattern can be obtained by printing the adhesive 82 onto the garment-facing surface of the absorbent article 80.

Figure 7:
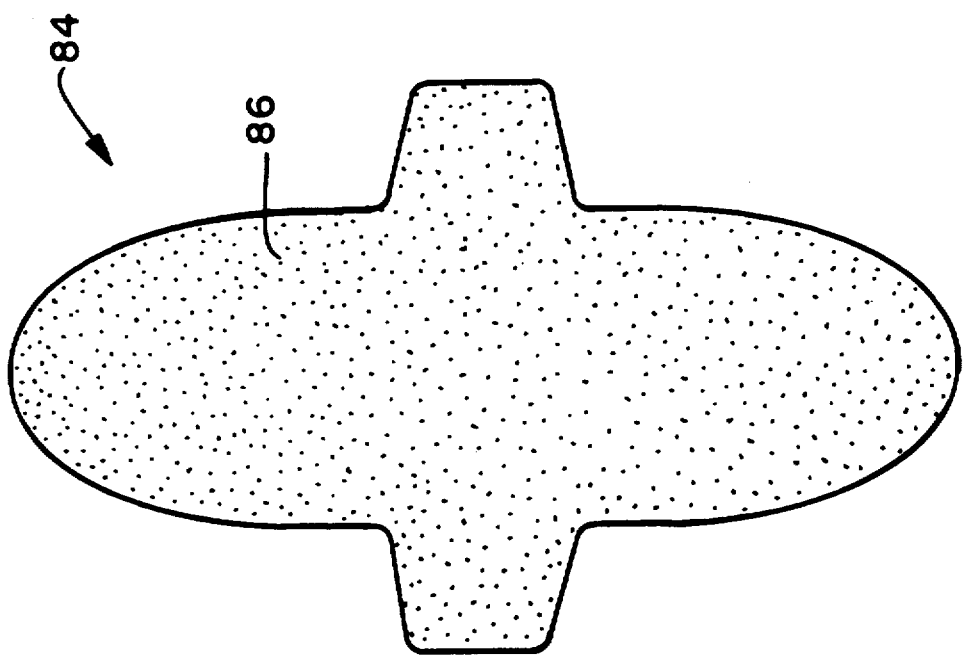
FIG. 7 is a bottom view of an absorbent article showing the entire bottom surface covered with a garment-attachment adhesive.

Referring to FIG. 7, an absorbent article 84 is shown having an oval-shaped central portion with a pair of relatively stiff tabs extending laterally outward from the longitudinal sides. In this particular embodiment, the entire garment-facing surface of the absorbent article 84 is covered by an adhesive 86. The adhesive 86 can be sprayed, painted, coated, rolled, or otherwise applied over the entire surface of the article 84. By using a single piece of release paper, it is now possible to coat the entire garment-facing surface of the article 84 with adhesive 86.

Figure 8:
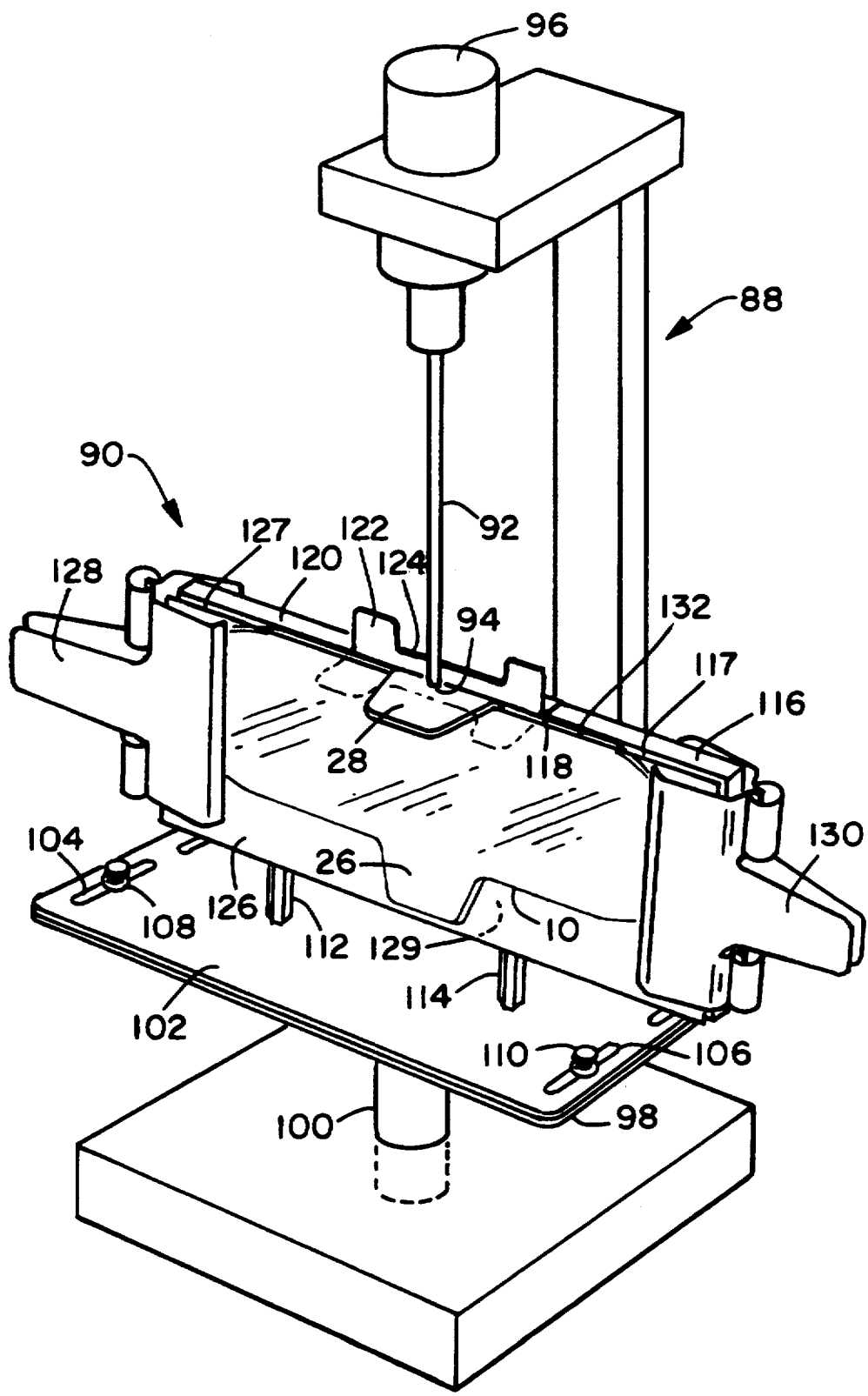
FIG. 8 is a perspective view of an apparatus designed to test the stiffness of the pair of tabs extending laterally outward from the absorbent article.

Referring to FIG. 8, a test instrument is shown for measuring the stiffness of the tabs which extend laterally outward from the longitudinal sides of the absorbent article. Since one of the novel features of this invention is using relatively stiff tabs which will not fold under their own weight when the release paper is removed, it is important that one can accurately measure tab stiffness. By using relatively stiff tabs, one can utilize a single piece of release paper.

In FIG. 8, an Instron tester 88 is shown containing a test apparatus 90. The Instron tester 88 is Model No. 1122 available from the Instron Corporation of Canton, Mass. The Instron tester 88 and the test apparatus 90 are used to quantify the term "stiffness" of each tab. The stiffness of each tab is defined as the ability of each tab to resist bending under an applied force. The bending stiffness of each tab is determined by measuring the peak force required to bend the tab through 90 degrees, starting from an initial position wherein the tab is perpendicularly aligned downward From the body-facing surface of the absorbent article.

The test apparatus 90 is designed to hold an absorbent article in a vertical position with one of its tabs positioned perpendicular to, and extending outward from, the body-facing surface 32. The test apparatus 90 is mounted on the Instron tester 88. A 0.25 inch (6 mm) diameter pin 92 having a smooth, rounded end 94 is attached to a 2,000 gram compression load cell 96 which is mounted in the top of the Instron tester 88. The pin 92 should have a length of 8 inches (203 mm) or longer, so various configuration tabs or flaps can be measured. The pin 92 can be moved downward toward the test sample at a predetermined speed. The speed of the descending pin 92 can be controlled by programming the Instron tester 88. The peak force required to independently bend each of the tabs through an angle of 90 degrees is measured in grams.

The test apparatus 90 includes a base plate 98 having a centrally located male stud 100 extending downward therefrom. The male stud 100 fits into an opening formed in the Instron tester 88. The test apparatus 90 also includes a flat plate 102 having a pair of slots 104 and 106 formed therethrough. Each slot 104 and 106 is located adjacent an end of the plate 102. The slots 104 and 106 receive a pair of screws 108 and 110 which pass down through the slots 104 and 106 and can enter screw holes or slots, not shown, which are formed in the base plate 98. The slots 104 and 106 and the screws 108 and 110 allow the flat plate 102 to be moved back and forth relative to the base plate 98 so that the test apparatus 90 can be aligned under the movable pin 92. Extending upward from the flat plate 102 are a pair of rods 112 and 114. The rods 112 and 114 support a vertical plate 116 containing a flat vertical surface 117. A hinge mechanism 118 is secured to an upper surface 120 of the vertical plate 116. The hinge mechanism 118 contains a movable portion 122 which can be rotated from a vertical position, wherein it is perpendicular with the upper surface 120, through 90 degrees to a position where it is parallel with the upper surface 120. The movable portion 122 has a large U-shaped cut-out 124 aligned along its transverse axis. The U-shaped cut-out 124 allows the pin 92 to move down past the hinge mechanism 118 and contact the tab being tested.

The test apparatus 90 further includes a flat plexiglass plate 126 having an upper surface 127 and an inner surface 129. The inner surface 129 is aligned parallel to the flat vertical surface 117 of the vertical plate 116 when holding a sample therebetween. The plexiglass 126 is approximately an ⅛ of an inch (about 3 mm) thick. The plexiglass plate 126 is designed to hold a test product flat against the vertical plate 116. The plexiglass plate 126 can be secured to the vertical plate 116 by a pair of clamps 128 and 130.

Test Procedure

The test procedure used to determine the stiffness of each tab on an absorbent article is as follows. First, the Instron tester 88 should be calibrated with the appropriate weight for the 2,000 gram compression load cell. Second, the pin 92 should also be checked to make sure it is not bent and that it can move downward at the desired speed and be able to pass beyond the end of each tab. Third, if the results are to be printed on graph paper, the supply of paper in the Instron should be checked. Fourth, if the Instron is connected to a digital readout mechanism, care should be taken to make sure everything is working properly. Fifth, the test apparatus 90 should be secured to the Instron tester 88 and aligned so as to hold a tab of the sample article in line and under the movable pin 92. Sixth, five samples of the absorbent articles are necessary to conduct the test. Each of the absorbent articles should have at least a pair of outwardly-extending side tabs or flaps. Seventh, before testing the articles, it is important that they be conditioned under TAPPI Standard Conditions. This requires that each absorbent article be conditioned for at least two hours at a temperature of 23.0° C.±1° C. and a relative humidity of 50.0 percent±2 percent.

It should be noted that both tabs on each sample are to be tested before subsequent samples are tested. This means that ten test values will be obtained for the five samples absorbent articles. Eight, each test measurement should be recorded and the ten values added to obtain a composite number. Ninth, this composite number is divided by the number of tabs tested to obtain an average stiffness value. The averaging of the ten test values provides a more realistic stiffness value and reduces error when comparing these values against the tab stiffness values of other products.

After the absorbent articles have been conditioned, the samples are tested one at a time. First, the release paper is removed. If several strips of release paper are present on the article, they should all be removed at this time. Second, the garment-attachment adhesive is then blocked by brushing the adhesive areas with talc powder. Talc powder, such as that available from the J. T. Baker Chemical Company of Phillipsburg, N.J., works well.

With the adhesive areas brushed with talc, the sample is then positioned with its body-facing surface against the vertical surface 117 of the vertical plate 116. The movable portion 122 of the hinge mechanism 118 should be in its vertical position to enable the sample to be positioned with a tab resting against the hinge mechanism 118. This means that an adjacent longitudinal side edge 132 of the sample will be flush with the upper surface 120 of the vertical plate 116, see FIG. 8. If the sample should have a non-linear or curved longitudinal edge, the sample should be positioned such that a straight line drawn between the two arcuate segments joining the base of the tab to the central absorbent portion is aligned with the upper surface 120 of the vertical plate 116. In determining the base of a tab, one should assume that the base of the tab starts on an extension line coaxially aligned with the longitudinal side edge of the sample. For Example, if the absorbent article contains a fringe portion formed from only the cover and the baffle, the outside edge of the fringe portion should be considered the longitudinal side edge of the sample.

The inner surface 129 of the plexiglass 126 is then positioned adjacent to the garment-facing surface of the sample and the plexiglass 126 is clamped to the vertical plate 116 by the clamps 128 and 130. The sample should now be flat and sandwiched between the vertical plate 116 and the plexiglass 126. At this time, the longitudinal side edge 132 of the sample should be checked to make sure it is even with the upper surface 120 of the vertical plate 116.

With the sample positioned as described above, the movable portion 122 of the hinge mechanism 118 is rotated downward 90 degrees causing the tab to be positioned perpendicularly outward from the vertical plate 116. Another way of stating this is that the tab 28 is rotated downward and outward 90 degrees from the body-facing surface 32 of the central portion 20 of the absorbent article 10. This will cause the tab 28 to be aligned perpendicularly to the pin 92. If the tab is so flexible that it tends to droop under its own weight, the starting position may be at an angle greater than 90°. This factor will not prevent the test from being conducted or from measuring the stiffness value of the tab.

The test apparatus 90 should be arranged such that the pin 92 will contact the body-facing surface of the tab 28 at a point which is 0.43±0.02 inches (11.0±0.5 mm) from the inner surface 129 of the plexiglass 126. It should be noted that, for thick samples greater than about 6 mm, the movable portion 122 of the hinge mechanism 118 should be sufficiently long to bend the tab at 90° relative to the body-facing surface 32 as described above. The test apparatus 90 should be checked out and aligned so that the pin 92 will contact the tab as described above. This will assure that the pin 92 will contact each tab at the same place on each of the samples. The pin 92 should be set at an initial gauge length of about 1 inch (about 25.4 mm) above the tab it will contact. The crosshead speed of the pin 92 should be set at 1,000 millimeters/minute. The total distance the pin 92 will travel downwards will vary upon the length and configuration of the tab. However, for each tab, the pin 92 should travel beyond the edge of the tab to assure that the tab has been bent through an angle of 90 degrees from its starting position. The pin 92 should be long enough to move down past the tab.

The peak force required to bend each tab 90 degrees is measured in grams. This value can be read directly off the graph paper by measuring the highest point of the curve plotted on the graph paper. It can also be automatically recorded and digitally displayed on a microprocessor unit, such as a Microcon II, which is available from the Instron Corporation.

Figure 9:
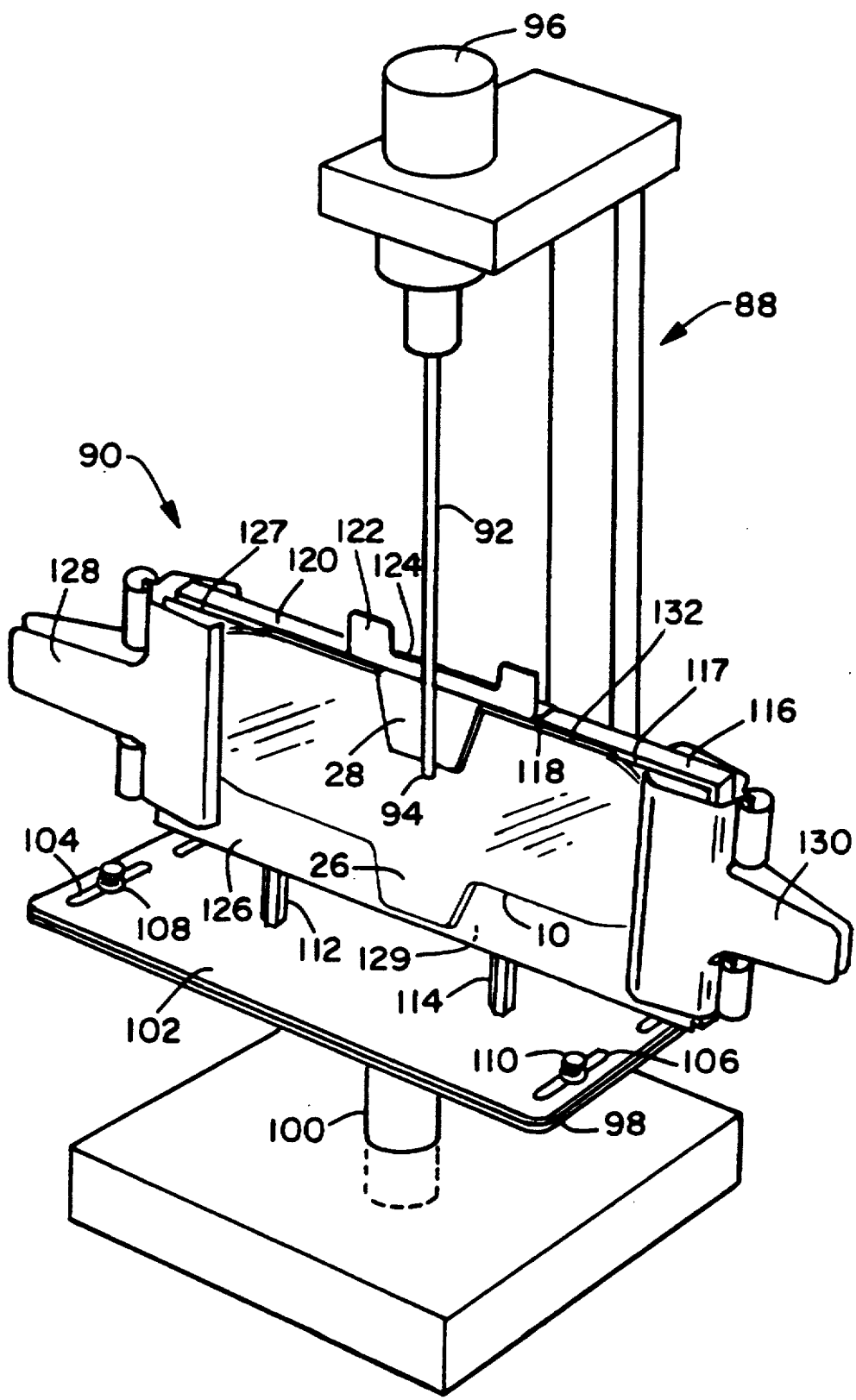
FIG. 9 is a perspective view of the apparatus depicted in FIG. 8 showing the pin in the down position.

Referring to FIG. 9, the Instron tester 88 is shown with the pin 92 in its down position extending a distance below the bottom edge of the bent tab. The distance should be about 0.25 to about 1 inch (about 6 mm to about 25.4 mm). The position of the bent tab is depicted, showing that it has been bent 90 degrees from its original position by the pin 92. This ending position is close to the position the tab will be in when it is attached to the exterior surface of the crotch portion of an undergarment.

The peak force required to bend the tab is recorded, and the pin 92 is then raised up to its initial starting position. The sample is then removed from the test apparatus 90 and positioned so that the opposite tab 26 can be tested. The stiffness of the opposite tab is then measured and recorded as explained above. The sample is then removed and the 2nd through 5th samples are tested in a similar fashion.

In Table 1 below, test results for some representative, thin absorbent articles, using the above-identified test procedure, are listed. The data indicates that the average peak force required to bend the tabs or flaps is relatively low. The highest average peak force for any of the three products is less than 5.6 grams.

TABLE 1

| Products | Test Data of Competitive Products | | | |
|---|---|---|---|---|
| | Ave. Peak Force (grams) | No. of Samples Tested | Range of Test Values | Avg. Thickness (in mm) |
| J&J's Stayfree Ultra Plus | 2.2 | 5 | 1.1–2.9 | 2.77 |
| J&J's Prima Light | 5.6 | 5 | 4.0–6.7 | 2.46 |
| P&G's Always Ultra Plus | 2.7 | 5 | 2.1–3.2 | 2.41 |

Table 2 shows the test results for four prototype panty liners with tabs. Each prototype included a polypropylene cover, a polyethylene baffle and an absorbent sandwiched therebetween. The absorbent was made from coform, but the weight and/or thickness varied. Each prototype also contained a release paper adhered to the baffle by a garment-attachment adhesive. Each of the prototypes measured 6.5 inches (165 mm) in length and 2.38 inches (60 mm) in width across the central portion of the absorbent as measured along the respective longitudinal and transverse axes. Each prototype panty liner contained two tabs, each measuring 1.58 inches (40 mm) in length (length being measured parallel to the longitudinal axis as described above) and 1 inch (25.4 mm) in width. The first three prototypes were made from coform having a basis weight of 190 grams per square meter (gsm). The fourth prototype was made from coform having a basis weight of 300 gsm. The weight of the cover and the absorbent were included in determining the basis weight.

The release paper was removed and the adhesive was blocked, as described above, before the thickness was measured. Five samples of each prototype were tested. The thickness of each sample was measured individually using a commercially available thickness indicator, Model No. 543-543-1 available from MTI Corporation, located at 18 Essex Road, Paramus, N.J. The article is placed on a flat plate with its body facing surface facing up. An acrylic block exerting a pressure of 2.13 grams per square centimeter was then placed over the body facing surface of the absorbent article. The movable pin on the thickness indicator was brought into contact with the acrylic block and the thickness measurement was read from the thickness indicator. This value was then recorded. The thickness values from each of the five samples were then totalled and divided by five to obtain an "average thickness." The "average thickness" values for the first three prototypes were 1.87 mm, 1.68 mm and 2.48 mm, respectively. The fourth prototype had an "average thickness" value of 2.95 mm.

Referring to the average peak force data in Table 2, it is shown that the peak force required to bend the tabs was relatively high. A high value indicates that the tabs are relatively stiff. Stiff tabs will not droop to any noticeable extent, under their own weight, when the release paper has been removed. The actual "average peak force" values ranged between 17.7 grams and 68.6 grams for the four products tested. Accordingly, the "average peak force" values tended to range from about 15 grams to about 70 grams. All of the "average peak force values" were well above those obtained for the products listed in Table 1. The actual individual values ranged between 13.6 and 99.3 grams. Accordingly, the peak force values tended to range from about 10 grams to about 100 grams.

TABLE 2

| | Panty Liners Made from Coform | | | |
|---|---|---|---|---|
| Prototypes | Avg. Peak Force (grams) | No. of Samples Tested | Range of Test Values | Avg. Thickness (mm) |
| 1 | 17.7 | 5 | 13.6–24.9 | 1.87 |
| 2 | 20.4 | 5 | 15.3–32.7 | 1.68 |
| 3 | 27.7 | 5 | 20.8–36.4 | 2.48 |
| 4 | 68.6 | 5 | 52.2–99.3 | 2.95 |

From the above data, it is evident that the prototype panty liners required an average peak force which was well above the average peak force values of the commercially available products listed in Table 1. The test results on the competitive products with flexible flaps had an "average peak force" value under 5.6 grams.

The importance of using an absorbent article with relatively stiff tabs is that, once the release paper has been removed, the tabs will not droop or fold downward and come in contact with another portion of the absorbent article. When a woman uses an absorbent article with stiff tabs, she can remove the release paper and attach the central portion of the article to the interior surface of the crotch portion of her undergarment, without the worry of having the adhesive located on the tabs from prematurely attaching to another part of the article. This allows the consumer to individually fold each tab around the elastic edge of the undergarment and attach it to the exterior surface of the crotch portion of her undergarment. A single piece of release paper allows the consumer to remove the release paper easily and quickly.

METHOD

The method of removing the absorbent article 10 from an undergarment 38 is also part of this invention. The absorbent article 10 has been described above. The central portion 20 is adhesively attached to an interior surface of a crotch portion of the undergarment 38 and the tabs 26 and 28 are folded around the elastic edges of the crotch portion of the undergarment 38 and are adhesively attached to an exterior surface thereof by the adhesive 42 and 44.

The absorbent article 10 is designed to be worn adjacent to the torso of a female body and in alignment with the vaginal opening. Once the absorbent article 10 has absorbed a sufficient quantity of body fluid, it has to be removed. Removal requires a lowering of the undergarment and undoing the adhesive bonds. Normally, each side flap is individually separated from the exterior surface of the undergarment before the central adhesive bond is broken and the article is removed.

The present absorbent article 10 can be removed from the undergarment using a much simpler and faster method. One method is for the consumer to grasp an end of the absorbent article 10 in one hand while holding a portion of her undergarment 38 in the other hand. She then pulls the absorbent article 10 upward, towards the opposite end, whereby the adhesive bonds are broken from the central portion 20 and from both of the tabs 26 and 28. The absorbent article 10 is then completely separated from the undergarment 38. It should be noted that the consumer can remove the article by either grabbing the front portion of the absorbent article 10 and pulling upward and backwards toward the opposite end, or she can grab the back end of the absorbent product and pull upward and forward towards the front end. The motion required to remove the absorbent article from the undergarment can be done in one continuous motion.

A second method of removing the absorbent article 10 from an undergarment is to remove one of the tabs and then lift the article 10 upward, away from the crotch portion of the undergarment. This sideways removal is facilitated by the presence of the short tabs 26 and 28. The shortness of the tabs 26 and 28, together with the small adhesive areas on each tab, attribute to this easy method of removal.

While the invention has been described in conjunction with several specific embodiments, it is to be understood that many alternatives, modifications, and variations will be apparent to those skilled in the art in light of the foregoing description. Accordingly, this invention is intended to embrace all such alternatives, modifications, and variations which fall within the spirit and scope of the appended claims.

We claim:
1. An absorbent article comprising:
 a) an absorbent having a central portion with longitudinally-extending. sides and a pair of relatively stiff tabs extending laterally outward from said longitudinal sides, said absorbent having a body-facing surface and a garment-facing surface, said tabs requiring a peak force of at least 20 grams to bend each of said tabs through an angle of 90° starting from a position wherein each of said tabs are aligned perpendicular to said body-facing surface; and
 b) means for securing said absorbent to an undergarment, said means being secured to said garment-facing surface and being present on both of said tabs.

2. The absorbent article of claim 1 wherein said tabs require a peak force of from about 20 to about 70 grams to bend said tabs through an angle of 90° starting from a position wherein said tabs are aligned perpendicular to said body-facing surface.

3. The absorbent article of claim 1 wherein said body-facing surface has a surface area of less than about 30 square inches and said article has a basis weight of less than about 400 grams per square meter.

4. An absorbent article comprising:
 a) a liquid-permeable cover;
 b) a liquid-impermeable baffle;
 c) an absorbent positioned between said cover and said baffle forming a pad having a central portion with longitudinally-extending sides and a pair of relatively stiff tabs extending laterally outward from said longitudinal sides, said pad having a body-facing surface, a garment-facing surface and a uniform thickness, said tabs requiring a peak force of at least 20 grams to bend each of said tabs through an angle of 90° starting from a position wherein each of said tabs are aligned perpendicular to said body-facing surface;
 d) attachment means for securing said pad to an undergarment, said attachment means being secured to said garment-facing surface and being present on both of said tabs; and
 e) release paper covering said attachment means.

5. The absorbent article of claim 4 wherein each of said tabs have a width dimension, measured parallel to a central transverse axis of said article, which prevent said tabs from contacting one another when said tabs are folded under said undergarment.

6. The absorbent article of claim 4 wherein a plurality of embossed lines extend downward from said body-facing surface into said absorbent to add integrity to said pad.

7. The absorbent article of claim 4 wherein each of said tabs is designed to be folded downward, along a line aligned parallel to each of said longitudinal sides, and each tab is to be secured to an exterior surface of said undergarment by said attachment means.

8. The absorbent article of claim 4 having a thickness of between about 1.5 to about 3.5 millimeters.

9. The absorbent article of claim 8 wherein said release paper and said pad have coterminous exterior peripheries.

10. The absorbent article of claim 4 wherein each of said tabs has a trapezoidal shape with length and width dimensions measured parallel to the longitudinal and transverse central axes of said article, respectively, each of said tabs having a maximum length of about 2.0 inches and a width of about 1.5 inches.

11. An absorbent article comprising:
 a) a liquid-permeable cover;
 b) a liquid-impermeable baffle;
 c) an absorbent positioned between said cover and said baffle forming a pad having a central portion with longitudinally-extending sides and a pair of relatively stiff tabs extending laterally outward from said longitudinal sides, said pad having a body-facing surface, a garment-facing surface and having a uniform thickness, said tabs requiring a peak force of at least 10 grams to bend each of said tabs through an angle of 90° starting from a position wherein each of said tabs is aligned perpendicular to said body-facing surface;

d) adhesive means for securing said pad to an undergarment, said adhesive means being located on said garment-facing surface with some of said adhesive being present on said central portion and some of said adhesive being present on each of said tabs; and e) release paper covering said adhesive means.

12. The absorbent article of claim 11 wherein said tabs, with said release paper removed, require a peak force of at least 10 to about 100 grams to bend each of said tabs through an angle of 90° starting from a position wherein each of said tabs is aligned perpendicular to said body-facing surface.

13. The absorbent article of claim 12 wherein said tabs, with said release paper removed, require a peak force of about 15 to about 70 grams to bend each of said tabs through an angle of 90° starting from a position wherein each of said tabs is aligned perpendicular to said body-facing surface.

14. The absorbent article of claim 11 wherein each of said tabs has a trapezoidal shape with length and width dimensions measured parallel to the longitudinal and transverse central axes of said article, respectively, each of said tabs having a maximum length of less than about 2.0 inches and a width of less than about 1.5 inches.

15. The absorbent article of claim 11 wherein, after removing said release paper, said tabs extend laterally outward from said longitudinal sides of said central portion.

16. The absorbent article of claim 11 wherein, after removing said release paper, said tabs extend outward from said longitudinal sides of said central portion and exhibit a droop of less than about 15° relative to said body-facing surface of said central portion.

17. The absorbent article of claim 11 wherein, after removing said release paper, said tabs maintain their original position with respect to said body-facing surface.

18. The absorbent article of claim 11 wherein said adhesive means covers a surface area of at least 0.5 square inches on each tab.

19. The absorbent article of claim 11 wherein at least 50% of the surface area of each tab is covered by adhesive.

20. The absorbent article of claim 11 wherein said adhesive extends the entire length of said tab, said length being measured parallel to the longitudinal central axis of said article.

21. An absorbent article comprising:

a) a liquid-permeable spunbond cover;

b) a liquid-impermeable polyethylene baffle;

c) an absorbent positioned between said cover and said baffle forming a pad having a central portion with longitudinally-extending sides and a pair of lateral tabs extending outward from said longitudinal sides, each of said tabs having a length less than about 25% of the length of said pad, said pad having a body-facing surface, a garment-facing surface and a uniform thickness, said tabs requiring a peak force of at least 20 grams to bend each of said tabs through an angle of 90° starting from a position wherein each of said tabs are aligned perpendicular to said body-facing surface;

d) adhesive means for securing said pad to an undergarment, said adhesive means being located on said garment-facing surface with some of said adhesive being present on said central portion and some of said adhesive being present on each of said tabs; and e) a single piece of release paper covering said adhesive means, said release paper having a periphery coterminous with an exterior periphery of said pad.

22. The absorbent article of claim 21 wherein said central portion has an elongated oval configuration.

23. The absorbent article of claim 21 wherein said central portion has an hourglass configuration.

24. The absorbent article of claim 21 wherein said central portion has a rectangular configuration.

25. The absorbent article of claim 21 wherein at least 50% of the surface area of each tab is covered by adhesive.

26. The absorbent article of claim 21 wherein approximately the entire surface area of each tab is covered by adhesive.

27. The absorbent article of claim 21 wherein a continuous embossed line is formed inward of the periphery of said pad to add integrity.

* * * * *

Adverse Decision In Interference

Patent No. 5,429,630, Chantelle M. Beal, Valerie V. Finch, Paul J. Serbiak, ABSORBENT ARTICLE AND A METHOD OF REMOVING SAID ARTICLE FROM AN UNDERGARMENT, Interference No. 103,951, final judgment adverse to the patentees rendered September 28, 2001, as to claims 1-27.

*(Official Gazette March 26, 2002)*